(12) United States Patent
Bhandari et al.

(10) Patent No.: US 8,865,288 B2
(45) Date of Patent: *Oct. 21, 2014

(54) MICRO-NEEDLE ARRAYS HAVING NON-PLANAR TIPS AND METHODS OF MANUFACTURE THEREOF

(75) Inventors: Rajmohan Bhandari, Salt Lake City, UT (US); Sandeep Negi, Salt Lake City, UT (US); Florian Solzbacher, Salt Lake City, UT (US); Richard A. Normann, Park City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 147 days.

This patent is subject to a terminal disclaimer.

(21) Appl. No.: 11/807,766

(22) Filed: May 29, 2007

(65) Prior Publication Data

US 2008/0138583 A1    Jun. 12, 2008

Related U.S. Application Data

(60) Provisional application No. 60/831,557, filed on Jul. 17, 2006.

(51) Int. Cl.
| | | |
|---|---|---|
| B32B 3/30 | (2006.01) | |
| B44C 1/22 | (2006.01) | |
| A61B 5/04 | (2006.01) | |
| H01L 21/77 | (2006.01) | |
| H01L 29/08 | (2006.01) | |
| A61M 37/00 | (2006.01) | |

(52) U.S. Cl.
CPC ... *A61M 37/0015* (2013.01); *A61M 2037/0053* (2013.01); *A61M 2037/0046* (2013.01)

USPC .............. 428/120; 428/172; 216/11; 216/52; 257/618; 257/623; 438/128; 600/372; 600/377; 600/393

(58) Field of Classification Search
USPC ............ 428/120, 172; 604/21, 171, 173, 191, 604/219, 264, 272; 600/393, 372, 377; 424/449; 216/11, 52; 438/128; 257/618, 623

See application file for complete search history.

(56) References Cited

U.S. PATENT DOCUMENTS

| 4,685,466 A | 8/1987 | Rau |
| 4,837,049 A | 6/1989 | Byers et al. |

(Continued)

FOREIGN PATENT DOCUMENTS

| WO | WO 2005/072630 | 8/2005 |
| WO | WO 2006/055799 | 5/2006 |

OTHER PUBLICATIONS

Jones, Kelly et al. "A glass/silicon composite intracortical electrode array", Annals of Biomedical Engineering, 1992, pp. 423-437, vol. 20.*

(Continued)

*Primary Examiner* — Donald J Loney
(74) *Attorney, Agent, or Firm* — Thorpe North & Western LLP

(57) ABSTRACT

A micro-needle array having tips disposed along a non-planar surface is formed by shaping the wafer surface into a non-planar surface to define the tips of the micro-needles. A plurality of trenches are cut into the wafer to form a plurality of columns having tops corresponding to the non-planar surface. The columns are rounded and sharpened by etching to form the micro-needles.

23 Claims, 6 Drawing Sheets

(56) References Cited

U.S. PATENT DOCUMENTS

| | | | |
|---|---|---|---|
| 4,969,468 A | 11/1990 | Byers et al. | |
| 5,215,088 A | 6/1993 | Normann et al. | |
| 5,286,944 A | 2/1994 | Li | |
| 5,388,577 A | 2/1995 | Hubbard | |
| 5,457,041 A | 10/1995 | Ginaven et al. | |
| 5,472,592 A | 12/1995 | Lowery | |
| 5,656,414 A | 8/1997 | Chou et al. | |
| 5,689,603 A | 11/1997 | Huth | |
| 5,838,715 A | 11/1998 | Corzine et al. | |
| 5,895,562 A | 4/1999 | Dubin | |
| 6,091,975 A | 7/2000 | Daddona et al. | |
| 6,285,446 B1 | 9/2001 | Farhadiroushan | |
| 6,334,856 B1 | 1/2002 | Allen et al. | |
| 6,406,638 B1 | 6/2002 | Stoeber et al. | |
| 6,511,463 B1 | 1/2003 | Wood et al. | |
| 6,551,849 B1 * | 4/2003 | Kenney | 438/34 |
| 6,622,035 B1 | 9/2003 | Merilainen et al. | |
| 6,702,950 B2 | 3/2004 | Moon et al. | |
| 6,730,444 B2 | 5/2004 | Bowes | |
| 6,743,211 B1 * | 6/2004 | Prausnitz et al. | 604/239 |
| 6,782,283 B2 | 8/2004 | Schmidt et al. | |
| 6,815,360 B1 | 11/2004 | Canham et al. | |
| 6,896,850 B2 | 5/2005 | Subramanian et al. | |
| 6,980,282 B2 | 12/2005 | Choi et al. | |
| 7,027,874 B1 | 4/2006 | Sawan et al. | |
| 7,118,942 B1 | 10/2006 | Li | |
| 7,212,851 B2 | 5/2007 | Donoghue et al. | |
| 7,240,416 B2 | 7/2007 | Milojevic et al. | |
| 7,332,197 B2 | 2/2008 | Wood et al. | |
| 7,712,198 B2 | 5/2010 | Kuo et al. | |
| 7,951,300 B2 | 5/2011 | Bhandari et al. | |
| 7,991,475 B1 | 8/2011 | Tang et al. | |
| 2002/0082543 A1 | 6/2002 | Park et al. | |
| 2003/0208138 A1 | 11/2003 | Olson | |
| 2004/0048419 A1 | 3/2004 | Kitamura et al. | |
| 2004/0082875 A1 | 4/2004 | Donoghue et al. | |
| 2004/0267205 A1 | 12/2004 | Stemme et al. | |
| 2005/0011858 A1 | 1/2005 | Kuo et al. | |
| 2005/0137531 A1 | 6/2005 | Prausnitz | |
| 2005/0171480 A1 | 8/2005 | Mukerjee et al. | |
| 2005/0258514 A1 * | 11/2005 | Smith et al. | 257/619 |
| 2006/0055090 A1 | 3/2006 | Lee et al. | |
| 2006/0110100 A1 | 5/2006 | Blauvelt et al. | |
| 2006/0127307 A1 | 6/2006 | Canham | |
| 2006/0135862 A1 | 6/2006 | Tootle et al. | |
| 2006/0173259 A1 | 8/2006 | Flaherty et al. | |
| 2007/0067007 A1 | 3/2007 | Schulman et al. | |
| 2007/0161964 A1 | 7/2007 | Yuzakov | |
| 2008/0102192 A1 | 5/2008 | Johnson et al. | |
| 2008/0125743 A1 | 5/2008 | Yuzhakov | |
| 2008/0138581 A1 | 6/2008 | Bhandari et al. | |
| 2008/0138582 A1 | 6/2008 | Bhandari et al. | |
| 2008/0262416 A1 | 10/2008 | Duan et al. | |
| 2008/0275400 A1 | 11/2008 | Ferguson | |
| 2009/0011158 A1 | 1/2009 | Yeshurun | |
| 2009/0099534 A1 | 4/2009 | Lee et al. | |
| 2009/0283425 A1 | 11/2009 | Clark et al. | |
| 2009/0301994 A1 | 12/2009 | Bhandari | |
| 2010/0041972 A1 | 2/2010 | Mason | |

OTHER PUBLICATIONS

Tsung-Kuan et al. "Fabrication of Out-of-Plane Curved surfaces in Si by Utilizing Rie Lag," IEEE, 2002, pp. 145-148.

Fofonoff, T. et al. Assembly-ready brain microelectrode array's In: Engineering in Medicine and Biology Society, Proceedings of the 25th Annual International Conference of the IEEE, 2003, pp. 1937-1940.

Fofonoff, T. et al. A highly flexible manufacturing technique for microelectrode array fabrication In: [Engineering in Medicine and Biology, 2002. 24th Annual Conference and the Annual Fall Meeting of the Biomedical Engineering Society] EMBS/BMES Conference, 2002, pp. 2107-2108.

Bhandari et al; A Novel Method of Fabrication Covoluted Shaped Electrode Arrays for Neural and Retinal Prostheses; Sensors and Actuators A; Nov. 4, 2007; pp. 123-130; vol. 145-146.

U.S. Appl. No. 12/464,691, filed May 12, 2009; Rajmohan Bhandari; office action issued Feb. 2, 2012.

Branner et al; Long Term Stimulation and Recording with a Penetration Microelectrode Array in Cat Sciatic Nerve; IEEE Transactions on Biomedical Engineering; vol. 51, No. 1; Jan. 2004.

Campbell et al.; A Silicon-Based, Three Dimensional Neural Interface: Manufacturing Process for an Intracortical Electrode Array; IEEE; Aug. 1991; pp. 758-768; vol. 38, No. 8.

Clark et al.; DARPA Revolutionizing Prosthetics 2009; Making It Work: Animal Physiology & Device Testing; Dept. of Bioengineering University of Utah Jun. 28, 2007; 5 pgs.

Dhillon et al.; Residual Function in Peripheral Nerve Stumps of Amputees: Implications for Neural Control of Artificial Limbs; The Journal of Hand Surgery; 2004; pp. 605-615.

Rakwal et al; Fabrication of Compliant High Aspect Ratio Silicon Microelectrode Arrays Using Micro-Wire Electrical Discharge Machining; Microsyst Technol; 2009; pp. 789-797; vol. 15.

Tajadod et al.; Electophoretic Photoresist Application for High Topography Wafer Surfaces; International Conference on Compound Semiconductor Mfg; 2003; 4 pgs.

Tathireddy et al; Fabrication of 3-Dimensional Silicon Microelectrode Arrays Using Micro Electro Discharge Machining for Neural Applications; Proc. Transducer'09, 15th Int. Conf. on Solid-State Sensors, Actuators and Microsystems, Denver, CO, Jun. 21-25, 2009, pp. 1206-1209.

Tathireddy et al; Towards High Aspect Ratio Tungsten Micro Electrode Array for Neural Recording and Stimulation Applications; 13th Annual International Function Electrical Stimulation (FES) Society Conference, Freiburg, Germany, Sep. 21-25, 2008.

U.S. Appl. No. 12/996,356, filed Dec. 3, 2010; Prashant Tathireddy.
U.S. Appl. No. 13/118,171, filed May 27, 2011; Rajmohan Bhandari.
U.S. Appl. No. 12/464,691, filed May 12, 2009; Rajmohan Bhandari; office action dated Feb. 7, 2013.
U.S. Appl. No. 11/807,766, filed May 29, 2007; Rajmohan Bhandari; office action dated Feb. 19, 2013.

* cited by examiner

MICRO-NEEDLE ARRAYS HAVING NON-PLANAR TIPS AND METHODS OF MANUFACTURE THEREOF

RELATED APPLICATIONS

This application claims the benefit of and hereby incorporates by reference U.S. Provisional Patent Application Ser. No. 60/831,557, filed Jul. 17, 2006, and entitled "An Integrated Wireless Neural Interface for Chronic Recording and Stimulation."

This application is also related to U.S. patent application Ser. No. 11/807,764, entitled "WAFER SCALE NEEDLE ARRAY", U.S. patent application Ser. No. 11/807,763, entitled "MASKING HIGH ASPECT-RATIO STRUCTURES", and U.S. Provisional Patent Application Ser. No. 60/932,232, entitled "MICRO-LENS ARRAYS AND CURVED SURFACE FABRICATION TECHNIQUES", each of which is filed concurrently herewith and which are hereby incorporated by reference.

GOVERNMENT RIGHTS

This invention was made with government support by the National Institutes of Health under Contract No. HHSN265200423621C and the Defense Advanced Research Projects Agency under Award No. 908164. The government has certain rights to this invention.

BACKGROUND

1. Field of the Invention

The present invention relates generally to needle array devices and methods of fabrication.

2. Related Art

The potential for implanting electronic devices into patients with direct interface to the neural system is vast. Systems which may enable paraplegics to regain control of their bladder or limbs, provide vision for the blind, or restore vocal cord function are all under development, and promising initial results have been obtained in some experiments.

A key component of some implantable systems is a needle array to enable interfacing of the electronics with a neuron or directly into brain tissue. For example, U.S. Pat. No. 5,215,088 to Normann et al. discloses a three-dimensional electrode device which can be used as a neural or cortical implant. The device of Norman, also known as the "Utah Electrode Array" (UEA), can be used to provide a neural interface to electronic equipment for sensing and/or stimulation.

SUMMARY

While much experimental success has been obtained with the UEA, some aspects of the UEA are less than optimum for long term implantation. For example, the UEA needle tips are disposed in a flat planar arrangement. Some potential applications of the UEA include interfacing to peripheral nerves and the retina, which are curved surfaces, and attempting to interface with the complex three-dimensional network of neurons within the brain. In such applications, a gap may be present between the array and the targeted neurons and/or tissue. This gap can result in connective tissue formation between the array and nerve that may reduce the quality of electrical connection and cause other potential problems.

Briefly, and in general terms, the invention is directed to needle arrays having the tips disposed in a non-planar arrangement and methods of manufacture of such arrays. In one embodiment, the invention includes a plurality of micro-needles disposed on a substrate, the tips of the micro-needles defining a non-planar tip surface. The tip surface may, for example, be concave, convex, or other non-planar surfaces. A method of manufacturing needle arrays, including wafer-scale fabrication is also disclosed.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 2(a)-2(f) is a series of illustrations of steps in fabricating a micro-needle array in accordance with an embodiment of the present invention, wherein FIG. 2(a) is a side view illustration of a wafer, FIG. 2(b) is a side view of the wafer after having a non-planar surface formed, FIG. 2(c) is a side view of the wafer after having a plurality of trenches cut, FIG. 2(d) is a top view of the wafer showing the tops of the plurality of columns, FIG. 2(e) is a top view of the wafer after dynamic etching showing the columns have been rounded, and FIG. 2(f) is a side view of the wafer showing the columns have been sharpened into micro-needles;

FIG. 4(a)-4(d) is a series of illustrations of steps in fabricating a micro-needle array with insulating material between the micro-needles in accordance with an embodiment of the present invention, wherein FIG. 4(a) is a side view of a wafer that has been sawed on the backside to form trenches, FIG. 4(b) shows the wafer with the trenches filled with insulating material, FIG. 4(c) shows the wafer after forming a non-planar surface on the front side and sawing a plurality of trenches into the front side; and FIG. 4(d) shows the wafer after etching has formed the micro-needle array.

DETAILED DESCRIPTION OF EXAMPLE EMBODIMENT(S)

In describing embodiments of the present invention, the following terminology will be used.

The singular forms "a," "an," and "the" include plural referents unless the context clearly dictates otherwise. Thus, for example, reference to "a needle" includes reference to one or more of such needles and "etching" refers to one or more of such processing steps.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "50-250 micrometers should be interpreted to include not only the explicitly recited values of about 50 micrometers and 250 micrometers, but also include individual values and sub-ranges within the indicated range. Thus, included in this numerical range are individual values such as 60, 70, and 80 micrometers, and sub-ranges such as from 50-100 micrometers, from 100-200, and from 100-250 micrometers, etc. This same principle applies to ranges reciting only one numerical value and should apply regardless of the breadth of the range or the characteristics being described.

As used herein, the term "about" means that dimensions, sizes, formulations, parameters, shapes and other quantities and characteristics are not and need not be exact, but may be approximated and/or larger or smaller, as desired, reflecting tolerances, conversion factors, rounding off, measurement error and the like and other factors known to those of skill in the art. Further, unless otherwise stated, the term "about" shall expressly include "exactly," consistent with the discussion above regarding ranges and numerical data.

Figure 1:
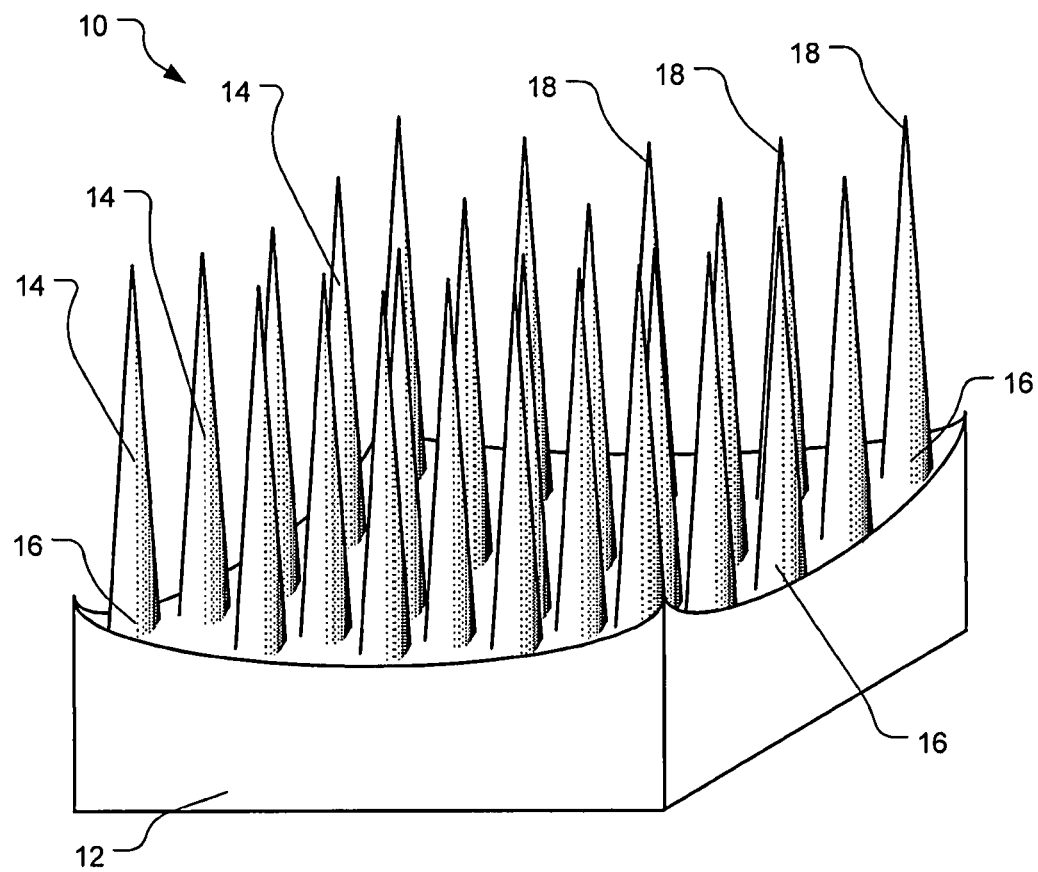
FIG. 1 is a perspective illustration of a micro-needle array having tips disposed along a non-planar surface in accordance with an embodiment of the present invention.

FIG. 1 illustrates a perspective view of a micro-needle array in accordance with an embodiment of the present invention. The micro-needle array 10 includes a substrate 12 and a plurality of spaced apart and substantially parallel micro-needles 14. The micro-needles each have a base 16 and a tip 18, the bases of the micro-needles being supported by the substrate. The tips of the micro-needles define a non-planar tip surface. In other words, the tips of the micro-needles vary across and form a non-planar surface. This non-planar surface can be formed by micro-needles having varying heights or uniform height micro-needles distributed on a non-planar substrate surface. For example, as shown in FIG. 1 the tips are arranged in a concave shaped surface, although other surface shapes can be provided as explained further below.

The micro-needles may also include a conductive coating disposed on the tips of the micro-needles to help provide a low impedance electrical connection from the tissue in which the needle array is inserted to the needle body. The coating may be, for example, one or more metals, designed to adhere to and provide an Ohmic contact to the material used for the needle body and designed to provide a stable interface when inserted in vivo. For example, for silicon micro-needles, a metal stack of titanium over platinum over iridium has been found to provide good performance. The titanium adheres well to silicon, the platinum provides a diffusion barrier, and the iridium provides a stable electric interface when inserted in vivo.

The micro-needle array may be encapsulated in a non-conductive, non-reactive material to help improve compatibility in vivo. For example, such materials can include parylene-C, silicon carbide and/or silicone. It will be appreciated that the tips can be left unencapsulated to allow electric contact between the micro-needles and the tissue into which the array is inserted.

The micro-needle array can be formed using various materials as will become more apparent from a discussion of fabrication techniques below. For example, the micro-needles and the substrate can be formed from silicon. As another example, the micro-needles can be formed of silicon or doped silicon and the substrate may be formed of glass.

As another alternative, the substrate may be a plastic material. More particularly, the substrate may be a biodegradable plastic, such as polycaprolactone (PCL), poly (DL-lactide-co-glycolide) or polyglycolide. The substrate helps to support the micro-needles during implantation. After implantation, the biodegradable plastic will dissolve, allowing the micro-needles to float in the tissue. This reduces mechanical coupling between the array and the tissue, helping to reduce neural damage.

Various geometric arrangements of the micro-needle array 10 can be used. For example, as shown in FIG. 1, the tips 18 can follow a concave surface, wherein tips near the center of the array are below tips near the edges of the array. The bases 16 may define a similarly concave surface depressed into the substrate 12, in which case the micro-needles 14 have similar lengths. As an alternative, the bases may define a planar surface, in which case the micro-needles near the center of the array are shorter than micro-needles near the edges of the array.

As another example, the tips 18 can define a convex surface, where tips near the center of the array extend upward relative to tips near the edges of the array. As yet another example, the tips 18 can be disposed in more complex surface shapes, having curvature in one dimension or two dimensions, depending on the number of sets of trenches that are cut. For example, one set of saw cuts can define curvature in one dimension (direction). A second saw set of saw cuts can define curvature in a second dimension, producing a three-dimensional surface shape. In other words, the height (or depth) of the curved surface z relative to a horizontal reference (e.g. the top surface of the wafer) can be described as a function $z=f(x, y)$ of the horizontal position x, y. Achievable surface shapes will be a function of the saw width, depth control (e.g., depth resolution), cutting angle control (e.g. vertical miter angle), rotational control of substrate (e.g. horizontal miter angle), etc.

The micro-needles 14 can be substantially parallel to each other. This can help to avoid tissue damage when the array is inserted into tissue, since lateral displacement of tissue by the micro-needles can be minimized by inserting the array into tissue in a direction aligned with the main axis of the micro-needles. In contrast, a micro-needle array formed by bending a flexible substrate may result in needles which are not parallel to each other. Such an array is more likely to cause tissue damage upon insertion in some applications. However, if desired, micro-needles 14 can be formed which are not parallel to each other as will become clear from the fabrication discussion below.

A method of fabricating an array of micro-needles will now be described in conjunction with FIG. 2(a)-FIG. 2(f). The method includes providing a wafer 22 as shown in side view in FIG. 2(a) from which the needle array is to be constructed. The wafer can be, for example, a mono-crystalline silicon wafer. Mono-crystalline silicon wafers are typically cut from a single crystal silicon ingot, for example as for integrated circuit manufacturing. It will be appreciated that the silicon wafer need not be perfectly single crystal, as most semiconductor grade silicon wafers contain a small number of defects of various types. Other wafer materials that can be used include ceramic material and polymers.

Figure 2A:
Figure 2B:
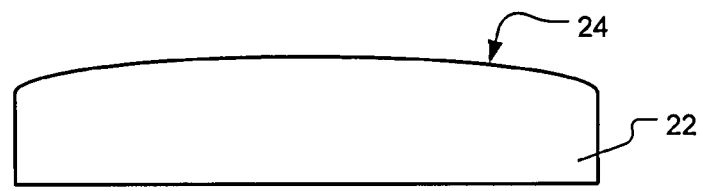

The method further includes shaping a top surface of the wafer 22 into a non-planar surface 24 as shown FIG. 2(b). For example, the top surface may be shaped by gray scale lithography. A gray scale mask creates three-dimensional structures within a photoresist layer than can be wet or dry etched to produce a curved surface. As another example, the non-planar surface may be formed by cutting a plurality of trenches of varying depth into the top surface, wherein the depth of the trenches corresponds to a non-planar surface and etching the top surface to remove material left between the trenches to form the non-planar surface as described in further detail below. The non-planar surface may be, for example, convex, concave, or other shapes.

Figure 2C:
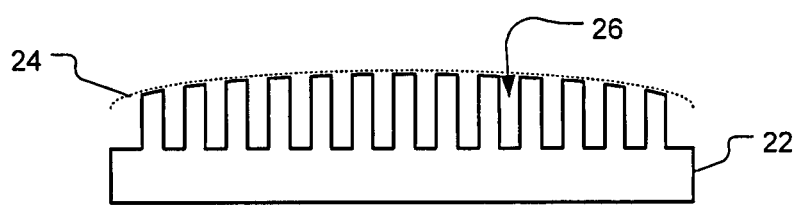
Figure 2D:
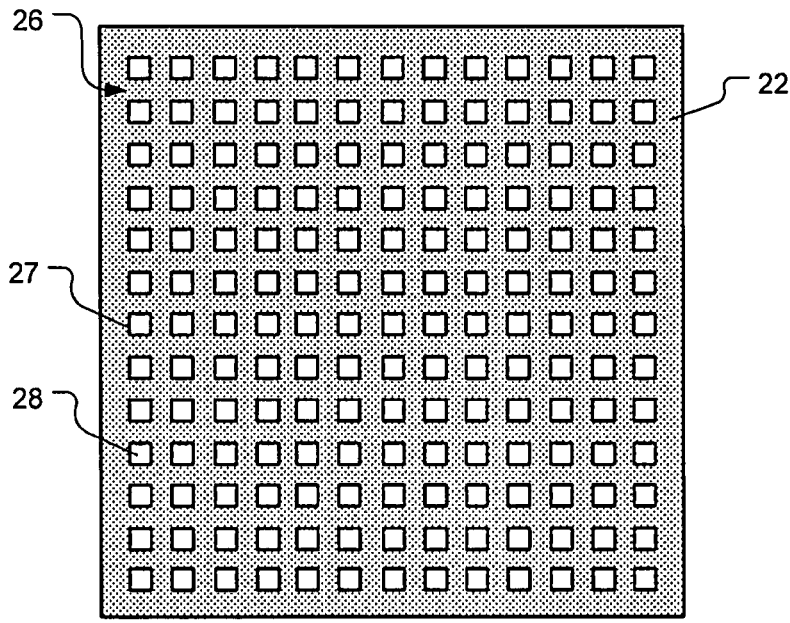

The non-planar surface 24 is cut into to form a plurality of trenches 26 as shown in top view in FIG. 2(c). Two sets of intersecting trenches are cut to form a plurality of columns 27 having tops 28 defined by the non-planar surface. For example, forming evenly spaced parallel saw cuts in one direction, turning the wafer 90 degrees, and forming a second set of evenly spaced parallel saw cuts, can produce a plurality of square columns as shown in FIG. 2(d). Alternately, spacing between the saw cuts can be varied to produce rectangular columns and different size square columns. More than one set of saw cuts can be used, for example, using three sets of saw cuts at 60 degrees relative to each other to form triangular or hexagonal shaped columns. The cutting can be performed, for example, using a saw (e.g. a programmable dicing saw). Other techniques for cutting the trenches may also be used, including for example deep reactive ion etching.

The method also includes etching the wafer to reshape the plurality of columns to round the columns and sharpen the tops into needle tips. For example, etching can be performed using a dynamic etch to round the columns and a static etch to form points at the tips of the columns.

Dynamic etching can be performed by placing the wafer into a holder and immersing the wafer in an etching solution. The holder can be constructed of a material which is resistant to the etching solution, such as polytetrafluoroethylene (e.g. Teflon®) or other polymers. The holder can include a gasket to help prevent contact between the back side of the wafer and the etching solution.

Figure 2E:
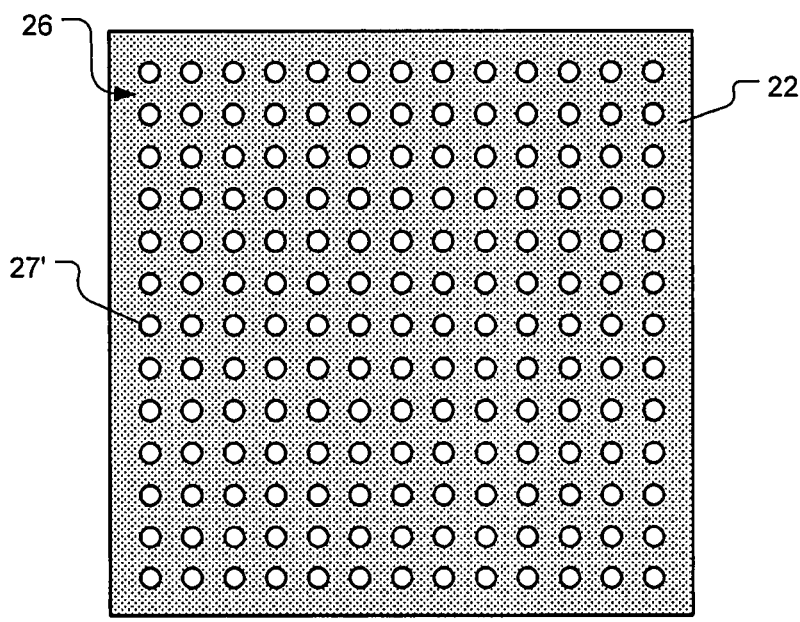
Figure 2F:
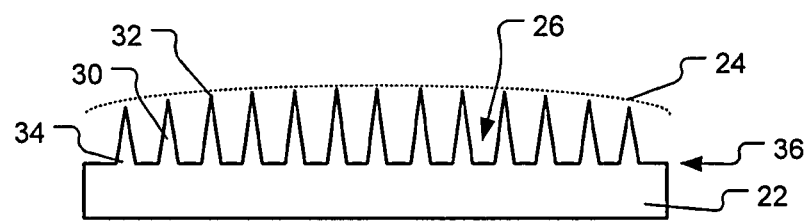

The immersed wafer is rotated in one direction, while a stirrer stirs the etching solution in an opposite direction to provide aggressive and continuous flow of fresh etching solution into the dicing kerfs. The size of the etching bath (size of the wafer), concentration of the etching solution, total volume of the etching solution, size of the stirring bar, distance between the stirring bar and wafer, rotation rates of the wafer and stirrer, and time of etching are all interrelated. Generally, for a larger stir-bar, less rotation of the stir bar is required to create a desirable vortex which drives a strong flush of etchant into the columns. For example, using an etching container of 7.5 inch diameter, a stirring bar of 3 inches length, and 2 inches of separation between the stirrer bar and wafer, it was found that rotating the wafer holder at about 22 rpm while counter rotating the stirrer bar at about 500 rpm provided good uniformity of the etching of the columns. Using a solution of 5% hydrofluoric acid (49% concentration) and 95% nitric acid (69% concentration), etching time of about 4 minutes reduces 250 micrometer square columns to round column of about 150 micrometers in diameter. As shown in FIG. 2(e), after the dynamic etching, the columns have been reshaped to a plurality of rounded columns 27' having substantially uniform cross section from base to tip, although there may be some narrowing of the columns toward the tip.

Static etching to sharpen the tips can be performed by inverting the holder to position the wafer columns in an upward direction and placing the wafer into etchant solution which is not stirred. In the static etching, the etching at the tips of the columns is faster than near the bases, because little fluid motion is present to replenish etching solution near to bottoms of the kerfs. This preferentially shapes the columns into micro-needles as shown in side view in FIG. 2(f). Using the same etching solution as described above, static etching can be performed for about 8 minutes. Longer etching tends to form more sharply pointed micro-needles, while shorter etching time tends to form more rounded, missile-shaped micro-needles. Etching time may be in the range of about 2 to about 20 minutes, although in general longer etching times tend to decrease uniformity.

The depth of the sawing can be constant so that the bottom of the trenches 26 define a plane 36. The bases 34 of the micro-needles 30 are thus disposed within a plane 36, and the micro-needles have varying length (height).

Figure 3:
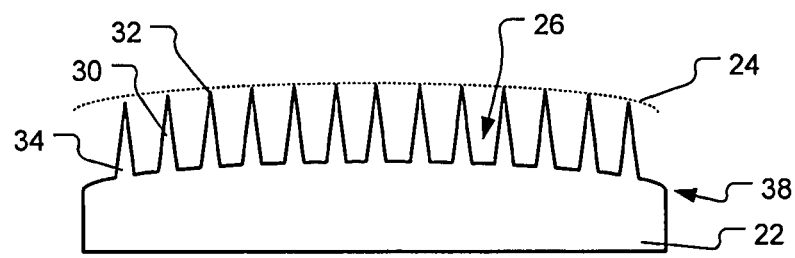
FIG. 3 is a side view illustration of a micro-needle array in accordance with another embodiment of the present invention.

Alternately, the depth of the cutting can be varied so that the bases 34 of the columns 27 define a second non-planar surface 38 as shown in FIG. 3. The depth of the cutting can be varied during forming of one set of parallel trenches to define a one-dimensional curve, or the depth can be varied during both sets of parallel trenches to define a two-dimensional curve. If the depth of the cutting follows the same profile as the (upper) non-planar surface 24, the needles will have substantially the same height.

It can be helpful to electrically insulate the needles from each other. This can be accomplished by cutting a third set of trenches into a back surface of the wafer, and filling the third set of trenches with an electrically insulating material. This operation can be performed before cutting the first set and the second set of trenches into the top side of the wafer. The first set and the second set of trenches can be cut sufficiently deeply into the top side of the wafer to intersect the third set of trenches (reaching the insulating material), thus removing all of the original wafer material between the columns that will be formed into the micro-needles. The insulating material can be, for example, glass. A glass frit can be disposed into the third set of trenches and then heating to melt and anneal the glass.

As another example, a polymer can be reflowed into the trenches. For example, biocompatible polymer, such as but not limited to benzo-cyclobutane (BCB), can be also be used as an insulating material between the electrodes. BCB can be selectively patterned on the trenches using standard lithographic techniques (e.g. spin coating and curing).

Figure 4A:
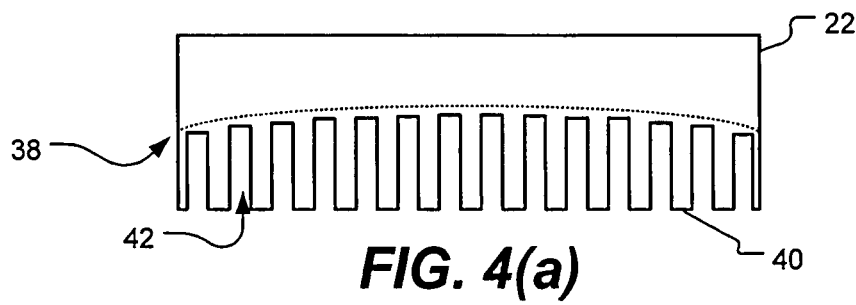
Figure 4B:
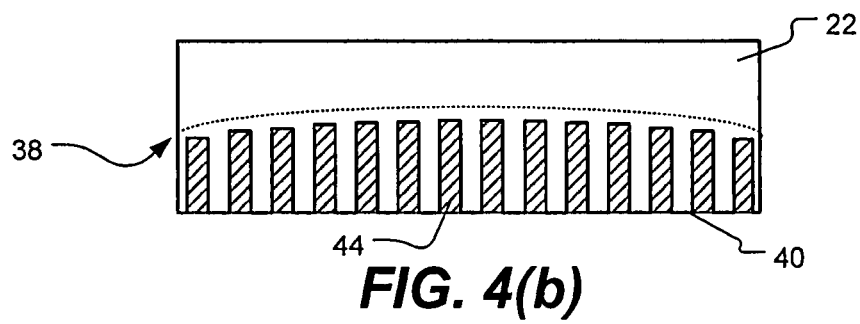
Figure 4C:
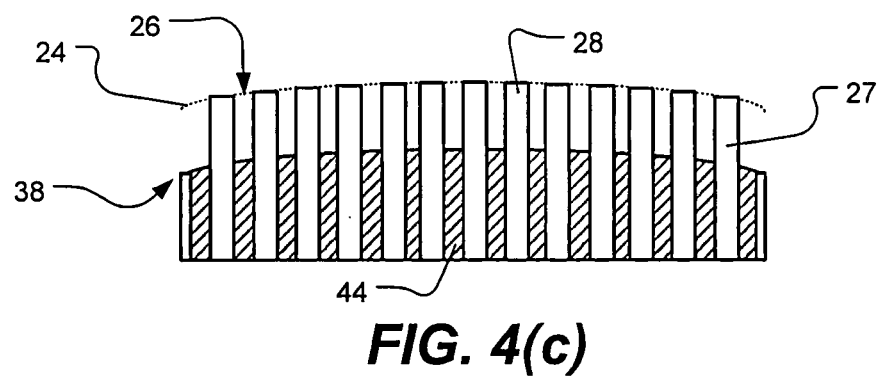
Figure 4D:
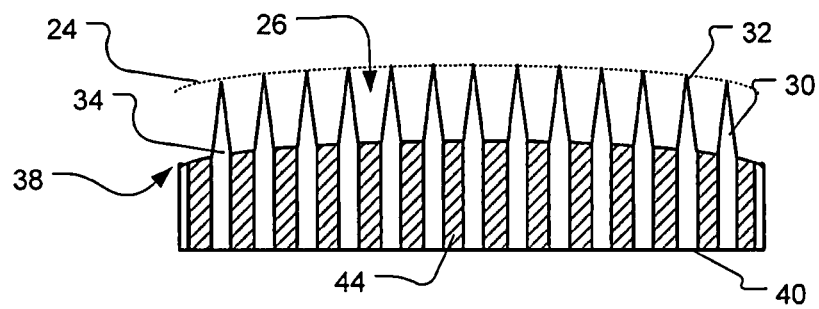
Figure 5:
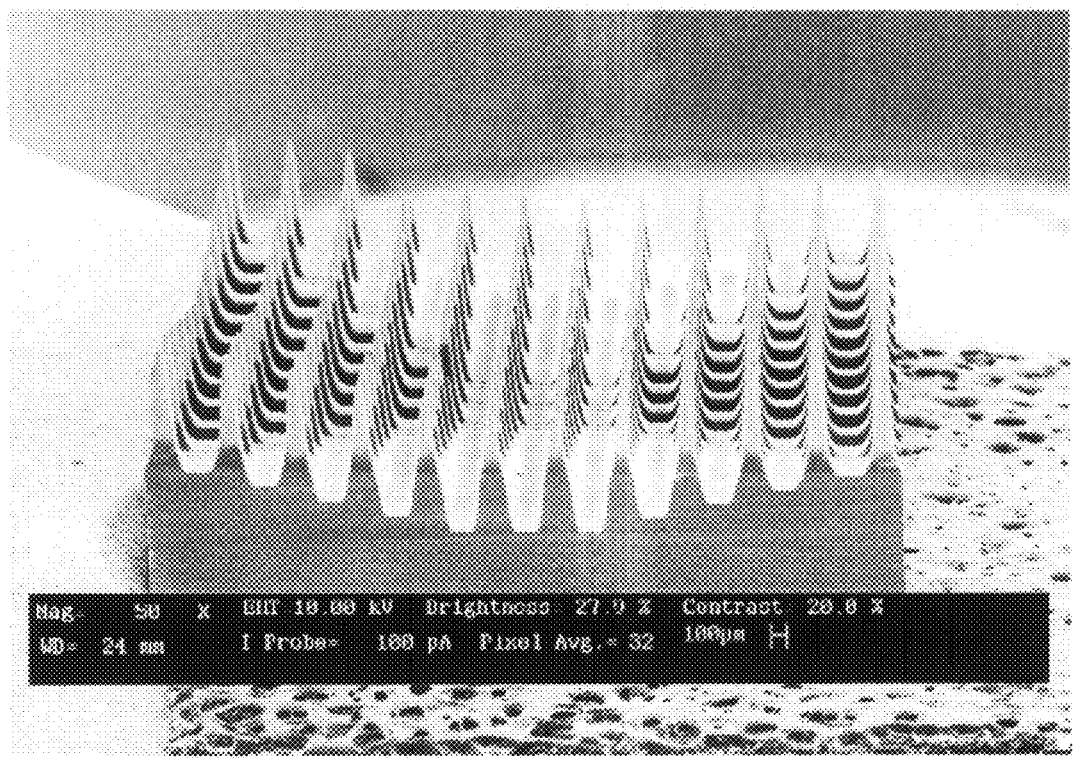
FIG. 5 is a scanning electron microscope picture of a micro-needle array having tips disposed in a convex non-planar surface in accordance with an embodiment of the present invention.

For example, FIG. 4(a)-FIG. 4(d) illustrate a sequence of steps to provide the insulating material between the needles. As shown in FIG. 4(a), the wafer 22 is initially sawed on the backside 40 to form a third plurality of trenches 42 corresponding to the desired base surface 38 profile of the micro-needles. The sawing can be fixed depth or variable depth, as for the front side. In FIG. 4(b) the trenches have been filled with insulating material 44. In FIG. 4(c), the front surface has been formed into a non-planar shape and the first and second plurality of trenches 26 cut from the front side to intersect the insulating material. This results in a plurality of columns 27 that are insulated from each other, the tops 28 defining a non-planar surface. The rounding and sharpening of the columns into micro-needles proceeds as described above to result in the finished micro-needle array illustrated in FIG. 4(d). FIG. 5 provides a scanning electron microscope image of an electrode array having a concave non-planar tip surface.

As mentioned above, non-planar surfaces can be formed by cutting trenches of varying depth into the surface of the wafer. The trenches define a non-planar or curved profile. The cutting can be performed mechanically, for example, using a dicing saw, leaving residual material between the trenches. The residual material can be removed using an isotropic etching to form the desired non-planar smooth surface. For example, silicon can be etched using a solution of hydrofluoric acid, as well as other known etchants. As another example, a mixture of hydrofluoric acid, nitric acid, acetic acid (HNA), and water is a useful etchant. It will be appreciated that the curved surface corresponds to the a desired surface profile, but may be displaced somewhat deeper into the wafer, since etching also removes some material from the substrate at the bottom of the trenches.

More than one plurality of trenches may be cut into the substrate to define a more complex profile. Just as one, two, three, or even more sets of trenches may be cut into the top-side to define complex non-planar surface profiles for the bases of the micro-needles, the same operations can be performed to define a non-planar surface profile for the tips of the micro-needles. Note that the profiles for the tips and bases need not be the same, although some variation in etching rate of the micro-needles may result under such conditions.

Although the illustrations and discussion above have assumed that the trenches are cut perpendicularly to the surface of the wafer being cut, this is not essential. If desired, trenches may be cut at an angle relative to vertical. Some non-planar surface profiles may be more efficiently fabricating by using a combination of angled cuts. It will also be appreciated that by using angled cuts, the columns formed need not be parallel, and accordingly can result in an array of needles that are not parallel to each other. For example, co-pending U.S. Provisional Patent Application Ser. No. 60/932,232, entitled "MICRO-LENS ARRAYS AND CURVED SURFACE FABRICATION TECHNIQUES", provides additional detail on a method for forming curved surfaces.

Various coatings may be applied to the micro-needles arrays. For example, metal coatings can be applied to the tips of the micro-needles to reduce the interconnect impedance between the micro-needle and tissue into which the micro-needle array is inserted. Biocompatible coatings, such as parylene-C and/or silicon carbide can be coated over the array. As a particular example, tips may be metallized, the array encapsulated in parylene-C, and then the tips of the array de-encapsulation to expose the tips. De-encapsulation may be performed using various techniques, including for example, shadow masking and laser ablation, plasma etching using masking techniques as disclosed in U.S. patent application Ser. No. 11/807,763, entitled "MASKING HIGH ASPECT-RATIO STRUCTURES", and other techniques as known in the art.

U.S. Patent Application Ser. No. 60/932,232, entitled "WAFER SCALE NEEDLE ARRAY", provides additional detail on methods for making wafer-scale needle arrays which can be applied in embodiments of the present invention.

A non-planar micro-electrode array can also be fabricated using a molding process using a micro-electrode array as fabricated above as a master. A polymer mold can be created from the non-planar micro-needle array by pouring polymer material on the micro-electrode array and curing the polymer material which takes on the inverted shape of the micro-needle array. The mold can be used to produce additional arrays, for example, by filling the mold with polymer material and curing, or electroplating metal onto the mold. Various polymers may be suitable for use in such an application, including for example poly-dimethy-siloxane (PDMS), polyesters, poly-tetra-fluoroethylene (PTFE), the SU-8 photo resist, and similar materials. An optional release agent can be used on the mold to facilitate release of molded arrays from the mold after forming is complete. In another optional embodiment, a pre-array can be formed which is approximately the shape of a desired non-planar micro-electrode array, but which requires further processing subsequent to molding. For example, at least a portion of dynamic and/or static etching steps can be performed subsequent to molding such that the pre-array may appear less rounded than typical final micro-needles. In this manner, more robust features can be molded with reduced likelihood of fracture during removal from the molds. The robust features can then be etched to from the desired micro-needle array.

Summarizing and reiterating to some extent, techniques for making micro-needle arrays having tips disposed in a non-planar surface have been described. The non-planar surface can be form specifically fitted for peripheral nerves, auditory nerves, retinal surfaces, etc. This enables the implanted micro-needle array to be secured around the nerve or surface and thus physically stabilized against displacement. This can help to avoid needing to seal the array to a nerve trunk (e.g. with sutures) helping to reduce neural damage. Further, electrode heights can be optimized to create localized electrical fields, making possible better selectivity in activating specific nerve regions.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention.

The invention claimed is:

1. A method of fabricating an array of micro-needles having tips disposed along a non-planar surface comprising:
   providing a wafer which is non-flexible;
   shaping a top surface of the wafer into a non-planar surface;
   cutting a first plurality of trenches into the non-planar surface, wherein the first plurality of trenches are uniformly spaced;
   cutting a second plurality of trenches into the non-planar surface to intersect the first plurality of trenches to form a plurality of columns having tops defined by the non-planar surface and wherein the second plurality of trenches are uniformly spaced such that the plurality of columns have a uniform width; and
   etching the plurality of columns to round the columns and sharpen the tops into needle tips to form the array of micro-needles such that tips of the micro-needles are disposed substantially along the non-planar surface, wherein the tip surface is a three-dimensional curve and the micro-needles are electrically conductive and electrically insulated from each other, and wherein the three-dimensional curve is a continuous function defined by $z=f(x,y)$ where z is a height of the micro-needles as a function of horizontal location x and y, and the micro-needles are solid throughout.

2. The method of claim 1 wherein at least one of cutting a first plurality of trenches and cutting a second plurality of trenches comprises varying a depth of the trenches so that bases of the columns define a second non-planar surface.

3. The method of claim 2 wherein cutting a first plurality of trenches and cutting a second plurality of trenches each comprise varying a depth of the trenches so that bases of the columns define a second non-planar surface.

4. The method of claim 1 wherein shaping the top surface of the wafer into the non-planar surface comprises:
   cutting a plurality of trenches of varying depth into the top surface, the depth of the trenches corresponding to the non-planar surface; and
   etching the top surface to remove material left between the trenches to form the non-planar surface.

5. The method of claim 1 wherein shaping a top surface of the wafer into a non-planar surface comprises forming a three-dimensional surface curved in two different directions.

6. The method of claim 1 wherein the first plurality of trenches and the second plurality of trenches are cut at angles of substantially 90 degrees to each other.

7. The method of claim 1 further comprising:
cutting a third plurality of trenches into a back surface of the wafer; and
filling the third plurality trenches with an insulating material.

8. The method of claim 7 wherein the insulating material is glass.

9. The method of claim 7 wherein cutting a plurality of trenches into a back surface of the wafer comprises varying depth of the trenches to correspond to the non-planar surface.

10. The method of claim 9 wherein cutting the first plurality of trenches into the non-planar surface and cutting the second plurality of trenches into the non-planar surface each comprise cutting to a depth sufficient to intersect the third plurality of trenches.

11. The method of claim 1 further using the wafer to form a mold.

12. The method of claim 1, wherein the three-dimensional curve is concave or convex.

13. A micro-needle array having tips disposed in a non-planar arrangement comprising:
a substrate which is non-flexible; and
a plurality of micro-needles each having a base and a tip, and are solid throughout each micro-needle, the bases of the micro-needles being supported by the substrate and the tips of the micro-needles defining a non-planar tip surface said tip surface being a three-dimensional curve which is a continuous function defined by $z=f(x,y)$ where z is a height of the micro-needles as a function of horizontal location x and y, wherein the micro-needles are electrically conductive and electrically insulated from each other.

14. The micro-needle array of claim 13, wherein the plurality of micro-needles are substantially parallel.

15. The micro-needle array of claim 13, wherein the substrate is formed of glass and the micro-needles are formed of silicon.

16. The micro-needle array of claim 13, wherein the substrate is formed of biodegradable plastic.

17. The micro-needle array of claim 13, further comprising a conductive coating disposed on the micro-needles.

18. The micro-needle array of claim 17, further comprising a non-conductive coating disposed over the conductive coating except at a tip portion of the micro-needles.

19. The micro-needle array of claim 13, wherein the substrate and the micro-needles are formed of a common material.

20. The micro-needle array of claim 13, wherein the bases of the micro-needles define a non-planar base surface.

21. The micro-needle array of claim 13, wherein the non-planar tip surface is convex.

22. The micro-needle array of claim 13, wherein the non-planar tip surface is concave.

23. The micro-needle array of claim 13, wherein the plurality of micro-needles have a uniform base width.

\* \* \* \* \*